(12) United States Patent
Panek, Jr.

(10) Patent No.: US 7,114,629 B2
(45) Date of Patent: Oct. 3, 2006

(54) MEDICAL WASTE DISPOSAL SYSTEM

(75) Inventor: Robert Joseph Panek, Jr., Huntley, IL (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 09/845,976

(22) Filed: Apr. 30, 2001

(65) Prior Publication Data

US 2002/0158068 A1 Oct. 31, 2002

(51) Int. Cl.
*B65F 1/04* (2006.01)
(52) U.S. Cl. .................. 220/345.1; 220/908; 220/260; 220/262; 220/23.87
(58) Field of Classification Search .............. 220/908, 220/262, 345.1, 348, 668, 23.83, 23.86, 23.87, 220/23.89, 23.91, 263, 264, 345.4, 908.1; 280/47.24, 47.26, 47.35
See application file for complete search history.

(56) References Cited

U.S. PATENT DOCUMENTS

| | | | | |
|---|---|---|---|---|
| 2,351,597 | A | | 6/1944 | Burlin |
| 2,634,933 | A | * | 4/1953 | Grimsley ................ 248/129 |
| 2,667,320 | A | | 1/1954 | Whitley |
| 3,041,030 | A | | 6/1962 | Heimrich |
| 3,064,931 | A | * | 11/1962 | Rowe ..................... 220/262 |
| 3,208,706 | A | | 9/1965 | Clark |
| 3,333,721 | A | * | 8/1967 | Marek |
| 3,347,507 | A | | 10/1967 | Dyer |
| 3,869,979 | A | * | 3/1975 | Sulcek .................... 220/908 |
| 4,338,987 | A | * | 7/1982 | Miles ..................... 144/285 |
| 4,420,168 | A | | 12/1983 | Dewing |
| 4,637,545 | A | * | 1/1987 | Stewart ................. 232/43.2 |
| 4,765,548 | A | | 8/1988 | Sing |
| 4,883,189 | A | | 11/1989 | Löbbert |
| 4,911,294 | A | * | 3/1990 | Russo et al. ............. 206/366 |
| 4,913,309 | A | * | 4/1990 | Fink ..................... 220/345.1 |
| 5,048,712 | A | | 9/1991 | Wolters |
| 5,082,132 | A | * | 1/1992 | Tsai ..................... 220/23.83 |
| 5,107,990 | A | | 4/1992 | Wicherski et al. |
| D326,753 | S | | 6/1992 | DeBusk |
| 5,143,389 | A | | 9/1992 | Jonkers |
| 5,163,574 | A | * | 11/1992 | Sosan ..................... 220/264 |
| D332,852 | S | | 1/1993 | Delmerico |
| 5,195,649 | A | | 3/1993 | Wolters |
| 5,230,525 | A | | 7/1993 | Delmerico et al. |
| 5,235,795 | A | * | 8/1993 | DeBusk .................. 53/467 |
| D341,237 | S | | 11/1993 | DeBusk |
| 5,348,222 | A | * | 9/1994 | Patey ..................... 220/262 |
| 5,354,023 | A | | 10/1994 | Meeks |

(Continued)

FOREIGN PATENT DOCUMENTS

DE 890623 * 9/1953 ................ 220/262

OTHER PUBLICATIONS

SharpsSafety brochure from Tyco Healthcare, Dec. 2000.*

(Continued)

*Primary Examiner*—Stephen Castellano
(74) *Attorney, Agent, or Firm*—RatnerPrestia

(57) ABSTRACT

A carrier is configured to hold a container having a door mounted for reciprocation between opened and closed positions. The carrier includes a body adapted to receive the container as well as an extension coupled for reciprocal movement with respect to the body. The extension is adapted for engagement with the door of the container, and the reciprocal movement of the extension is adapted to reciprocate the door of the container between the opened and closed position. A container system including a container and the carrier is also provided.

21 Claims, 13 Drawing Sheets

U.S. PATENT DOCUMENTS

| | | |
|---|---|---|
| D352,350 S | 11/1994 | Rambo et al. |
| 5,372,271 A | 12/1994 | Miller et al. |
| D358,240 S | 5/1995 | Mosior |
| 5,415,315 A | 5/1995 | Ramirez |
| 5,419,435 A * | 5/1995 | Perzan et al. ................ 206/366 |
| 5,474,201 A | 12/1995 | Liu |
| 5,531,346 A * | 7/1996 | Mosior ....................... 220/908 |
| 5,531,348 A * | 7/1996 | Baker et al. ................ 220/908 |
| 5,538,158 A | 7/1996 | Prout et al. |
| 5,570,547 A * | 11/1996 | Webb et al. .................. 52/194 |
| 5,582,322 A | 12/1996 | Prout et al. |
| 5,590,840 A * | 1/1997 | Adams et al. ................ 241/99 |
| 5,659,247 A * | 8/1997 | Clements .................... 324/239 |
| 5,671,859 A | 9/1997 | Sheu et al. |
| 5,673,811 A * | 10/1997 | Dickinson et al. .......... 220/812 |
| D388,577 S | 12/1997 | Rehrig et al. |
| 5,730,451 A | 3/1998 | Walker |
| D393,334 S | 4/1998 | Presnell et al. |
| 5,881,896 A | 3/1999 | Presnell et al. |
| 5,899,468 A | 5/1999 | Apps et al. |
| 5,947,285 A * | 9/1999 | Gaba et al. .................. 206/366 |
| 6,010,024 A | 1/2000 | Wang |
| 6,053,354 A | 4/2000 | Niemeyer |
| 6,138,558 A * | 10/2000 | Harrington .................. 100/102 |
| 6,202,922 B1 * | 3/2001 | Phillips et al. ............. 232/43.1 |
| D445,228 S | 7/2001 | Apps et al. |
| D478,701 S | 8/2003 | Panek, Jr. |
| 6,623,316 B1 | 9/2003 | Wu |
| 6,626,316 B1 | 9/2003 | Yang |
| 6,626,321 B1 | 9/2003 | Jaeger |
| 6,651,992 B1 | 11/2003 | Smith, Sr. |
| 6,722,672 B1 | 4/2004 | Cates et al. |
| 2002/0158068 A1 | 10/2002 | Panek, Jr. |
| 2004/0020927 A1 | 2/2004 | Yang et al. |

OTHER PUBLICATIONS

SHARPSAFETY Brochure of Tyco Healthcare, dated Dec. 2000.

* cited by examiner

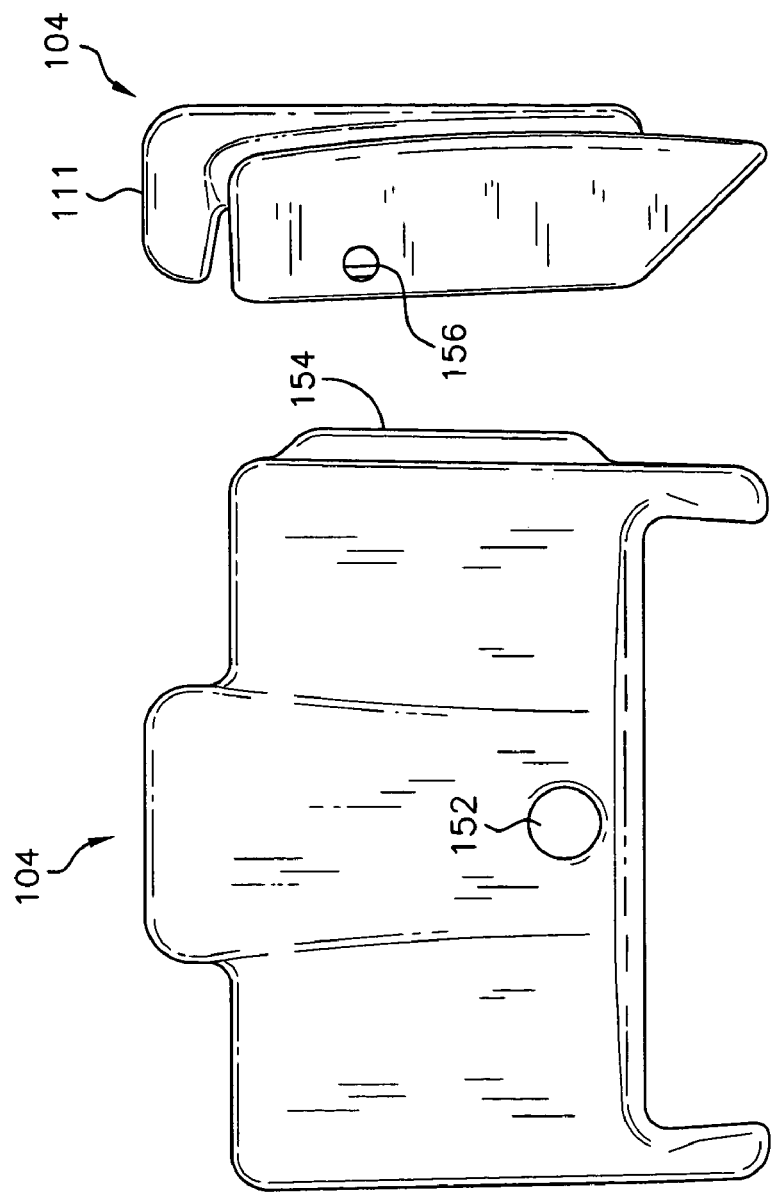
FIG. 6C
FIG. 6A
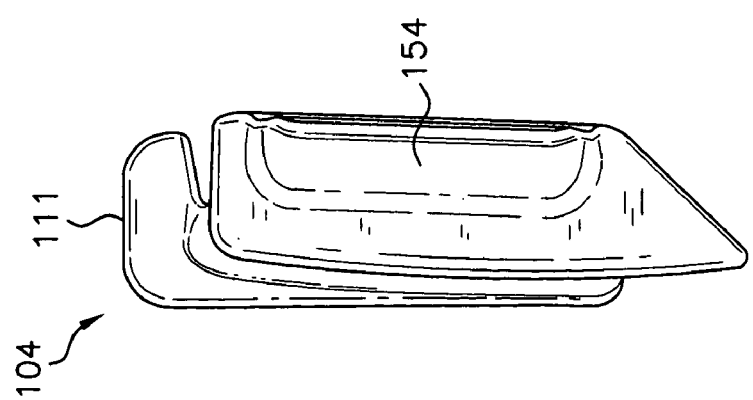
FIG. 6B

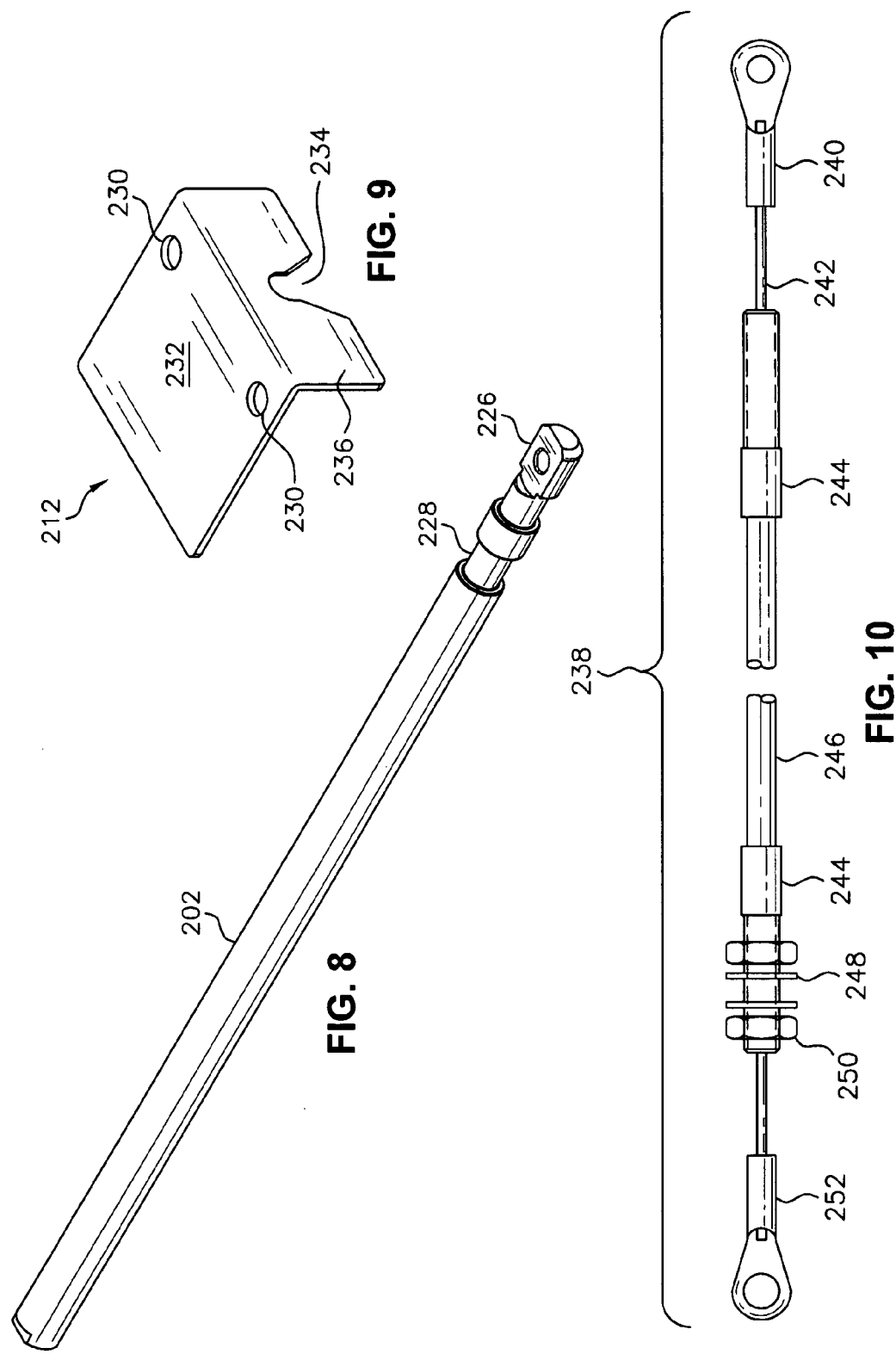

MEDICAL WASTE DISPOSAL SYSTEM

FIELD OF THE INVENTION

This invention relates generally to the disposal of contaminated items and, in particular, to a system for use in a hospital or a similar environment where contaminated items are to be collected and disposed of without creating a hazard for patients or hospital personnel.

BACKGROUND OF THE INVENTION

In hospitals, clinics and similar medical institutions, contamination continues to be of upmost concern. The prevention of the spread of communicable diseases is a major priority; therefore, disposable, single-use, patient care products have become prevalent.

Such patient care products are contaminated, once used, and can transmit disease. These patient care products include devices such as hypodermic needles, intravenous needles, lasers, scalpel blades or other sharps—all of which are required to be disposed at their point of usage under current guidelines of the United States Centers for Disease Control.

Various disposal containers for medical waste have been proposed for the purpose of preventing individuals from gaining access to contaminated items, such as sharps, once the waste has been deposited into the container. For example, a waste container having a top with a slidable closure is disclosed by Mosior in U.S. Pat. No. 5,531,346. The top of the waste container disclosed by Mosior has an access aperture, and the slidable closure on the top is positioned to slide between opened and closed positions. The closure includes a handle to facilitate sliding movement of the closure. The closure disclosed by Mosior can be temporarily retained in a first closed position over the aperture, and can be permanently retained in a second closed position over the aperture.

A protective container is disclosed by Marek in U.S. Pat. No. 3,333,721. A removable cover of the container disclosed by Marek is interlockable with panels of the container, and the removable cover has a door opening and a slidable door positioned under the cover. The door of the container disclosed by Marek is moved by means of a cable that passes through the cover and is fastened at its lower end to a footpedal.

Despite these proposed containers, there remains a need, however, for an improved medical waste disposal system that can further reduce the chance of contact between the medical personnel and the medical waste and to help prevent unauthorized access to medical waste held within the container.

SUMMARY OF THE INVENTION

The present invention provides a carrier that is configured to hold a container having a door mounted for reciprocation between opened and closed positions. The carrier includes a body that is adapted to receive the container. The carrier also includes an extension that is coupled for reciprocal movement with respect to the body of the carrier. The extension is adapted for engagement with the door of the container. The reciprocal movement of the extension is adapted to reciprocate the door of the container between the opened and closed positions.

The present invention also provides a container system having the container and the carrier.

BRIEF DESCRIPTION OF THE DRAWING

The invention is best understood from the following detailed description when read in connection with the accompanying drawing. It is emphasized, according to common practice, that various features illustrated in the drawing are not to scale. On the contrary, the dimensions of the various features are arbitrarily expanded or reduced for clarity. Included in the drawing are the following figures:

FIG. 6A is a top view of an embodiment of a hood component of the container system illustrated in FIG. 1.

FIG. 6B is a right side view of the hood component illustrated in FIG. 6A.

FIG. 6C is left side view of the hood component illustrated in FIG. 6A.

FIG. 8 is a perspective view of an embodiment of an extension or arm component of the arm control assembly illustrated in FIG. 7.

FIG. 9 is a perspective view of a locking member component of the arm control assembly illustrated in FIG. 7.

FIG. 10 is a plan view of an embodiment of a cable assembly adapted for use in the container system illustrated in FIG. 1.

DETAILED DESCRIPTION OF THE INVENTION

Figure 1:
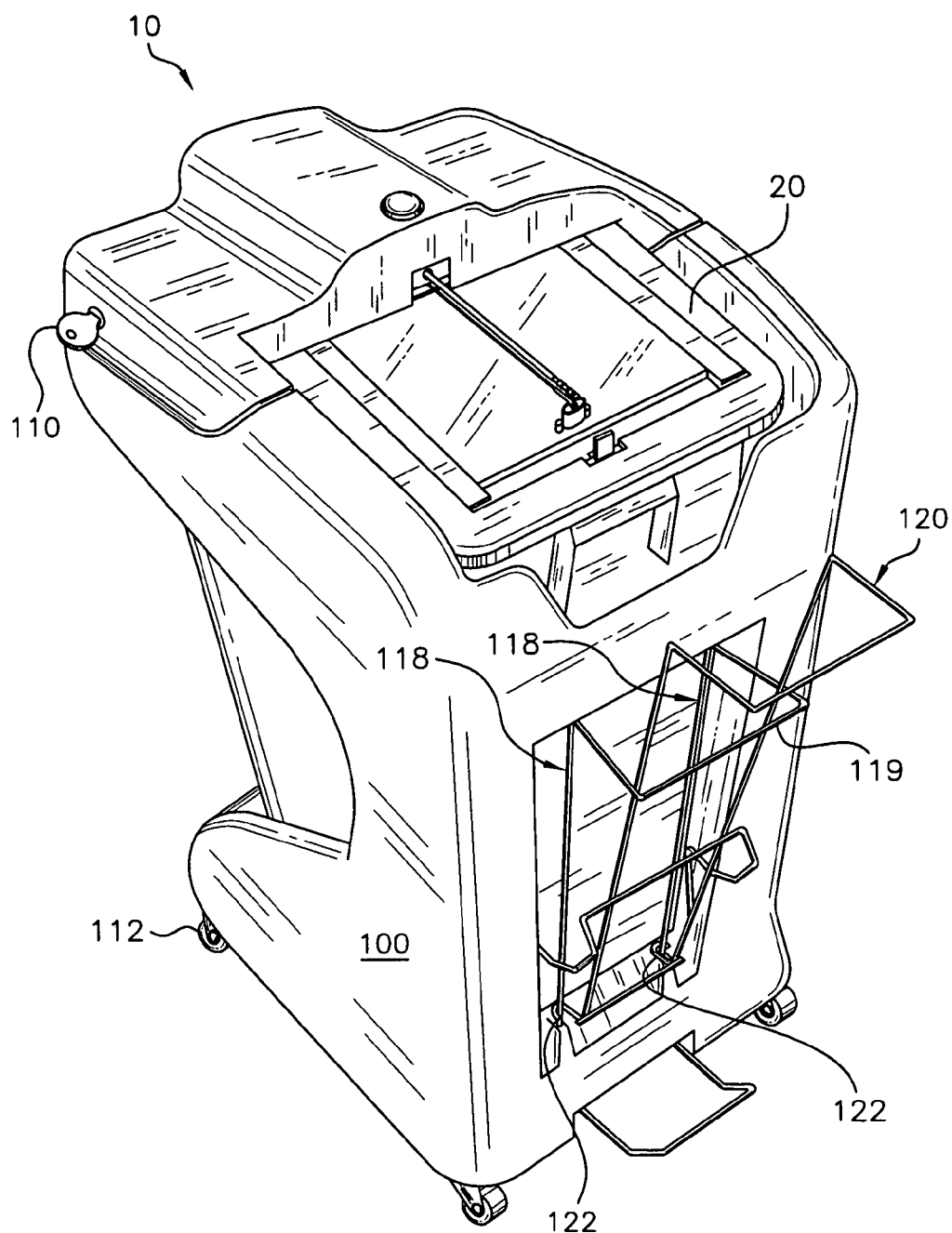
FIG. 1 is a perspective view of an embodiment of a container system according to this invention.

Exemplary details of this invention will now be described with reference to preferred embodiments selected for illustration in the Figures. It will be appreciated that the Figures have not been rendered to any particular scale or proportion. Also, it will be appreciated that the scope of this invention is not limited to the embodiments selected for illustration in the Figures. Instead, the scope of this invention is defined separately in the appended claims.

Generally, referring to the Figures, this invention provides a carrier 100 that is configured to hold a medical waste container 20 having a door 26 mounted for reciprocation between opened and closed positions. The carrier 100 includes a body 105 that is adapted to receive the medical waste container 20. The carrier 100 also includes an extension or arm 202 coupled for reciprocal movement with respect to the body 105. The arm 202 is adapted for engagement with the door 26 of the medical waste container 20. The reciprocal movement of the arm 202 is adapted to reciprocate the door 26 of the medical waste container 20 between the opened and closed positions.

This invention also provides a container system 10 including the medical waste container 20 in combination with the carrier 100. The system 10 has been discovered to reduce contact between medical professionals and the medical waste container 20 during use. The system 10 has also been discovered to resist unauthorized use of, and unintended access to the interior of, the medical waste container 20.

Referring specifically to FIG. 1, the medical waste container system 10 includes a carrier 100 that can receive the medical waste container 20. The carrier 100 includes several features to facilitate the mobility of the medical waste container system 10. Specifically, the carrier 100 includes four (4) wheels 112 mounted at the base of the carrier 100 so that the medical waste container system 10 can easily and readily be transported from one position to another by a user of the system 10. Two (2) of the four (4) wheels 112 are preferably lockable so that movement of the system 10 along the ground can be prevented or controlled.

Also, an extendable handle 120 extends upwardly and outwardly from the carrier 100 so that the container system 10 can be pulled by a user. More specifically, the handle 120 is formed from thick metallic wire formed into an elongated loop that terminates at its base with a pair of loops 122. Those loops 122 engage a pair of vertically-extending handle guides 118 which are fixed to the body of the carrier 100. A loop 119 extends between the handle guides 118 toward the top portion of the handle guides 118, thereby forming a support against which the upper portion of the handle 120 rests.

It will be understood that the handle 120 can be extended upwardly and outwardly with respect to the carrier 100 by virtue of the sliding relationship between the loops 122 at the base of the handle 120 and the handle guides 118 to which the loops 122 are slidingly engaged. As the handle loops 122 slide upwardly along the handle guides 118, the handle 120 extends upwardly and outwardly with respect to the carrier 100, while still resting against the loop 119 toward the top of the handle guides 118. When in this extended position, a user of the system 10 can easily move the carrier 100 from one location to another. When finished, the user can release the handle 120 to the retracted position as the loops 122 at the base of the handle 120 slide downwardly along the handle guides 118.

Figure 2:
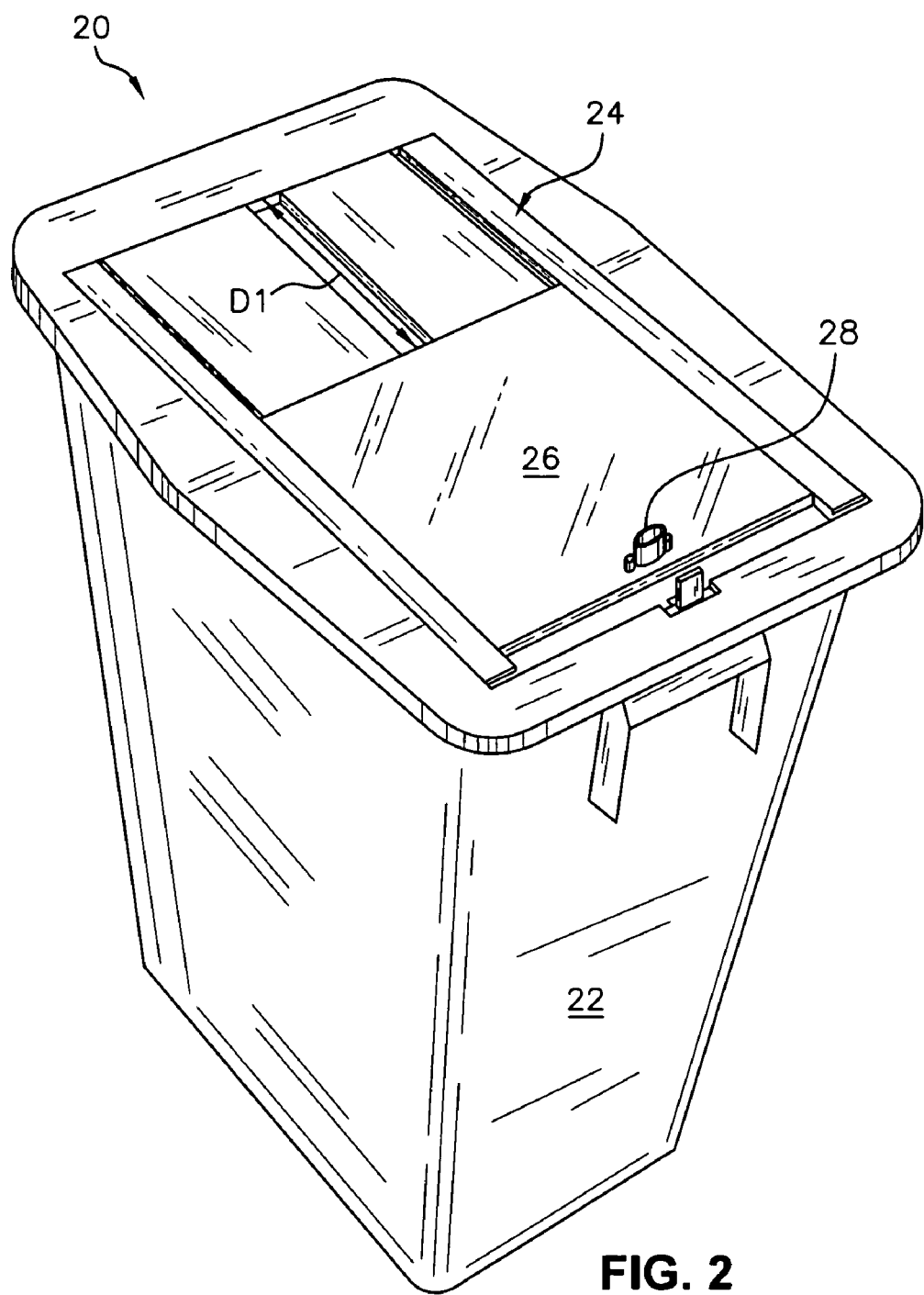
FIG. 2 is a perspective view of a container than can be used as a component of the container system illustrated in FIG. 1.

Referring now to FIG. 2, a preferred embodiment of a medical waste container 20 is illustrated, which container can be used in the medical waste container system 10 illustrated in FIG. 1. An exemplary waste container is disclosed by Mosior in U.S. Pat. No. 5,531,346, which is incorporated herein by reference. An exemplary waste container is also available from Tyco Healthcare Group LP of Mansfield, Mass. (see, e.g., Product Nos. 8938, 8998S, 8935, 8936SA, 8939 and 8934).

The medical waste container 20 includes a receptacle 22 on which a lid 24 is engaged. A door 26 is mounted for sliding reciprocation with respect to the lid 24. More specifically, the door 26 slides with respect to the lid 24 in the direction indicated by the arrow labeled D1. In FIG. 2, the door 26 is shown in the closed position. As the door 26 slides in the direction D1, the door 26 moves from the closed position (as illustrated) to an opened position (not shown in FIG. 1). When the door 26 is in the closed position, access to the interior of the medical waste container 20 is prevented. Conversely, when the door 26 is in the opened position, access is provided to the interior of the receptacle 22 so that medical waste can be inserted for disposal.

It will be understood that the medical waste container system 10 illustrated in FIG. 1, helps to reduce contact between the user of the system 10 and the medical waste container 20. More specifically, as will be described later in further detail, is no longer necessary for the user of the system 10 to make hand contact with the door 26 of the medical waste container 20 in order to open the container 20 and gain access to the interior of the receptacle 22 (in order to discard medical waste) or to close the door 26 to prevent such access. Also, the medical waste container system 10 makes it possible to prevent unauthorized or inadvertent access to the interior of the medical waste container 20, as will be described later in further detail.

Figure 3:
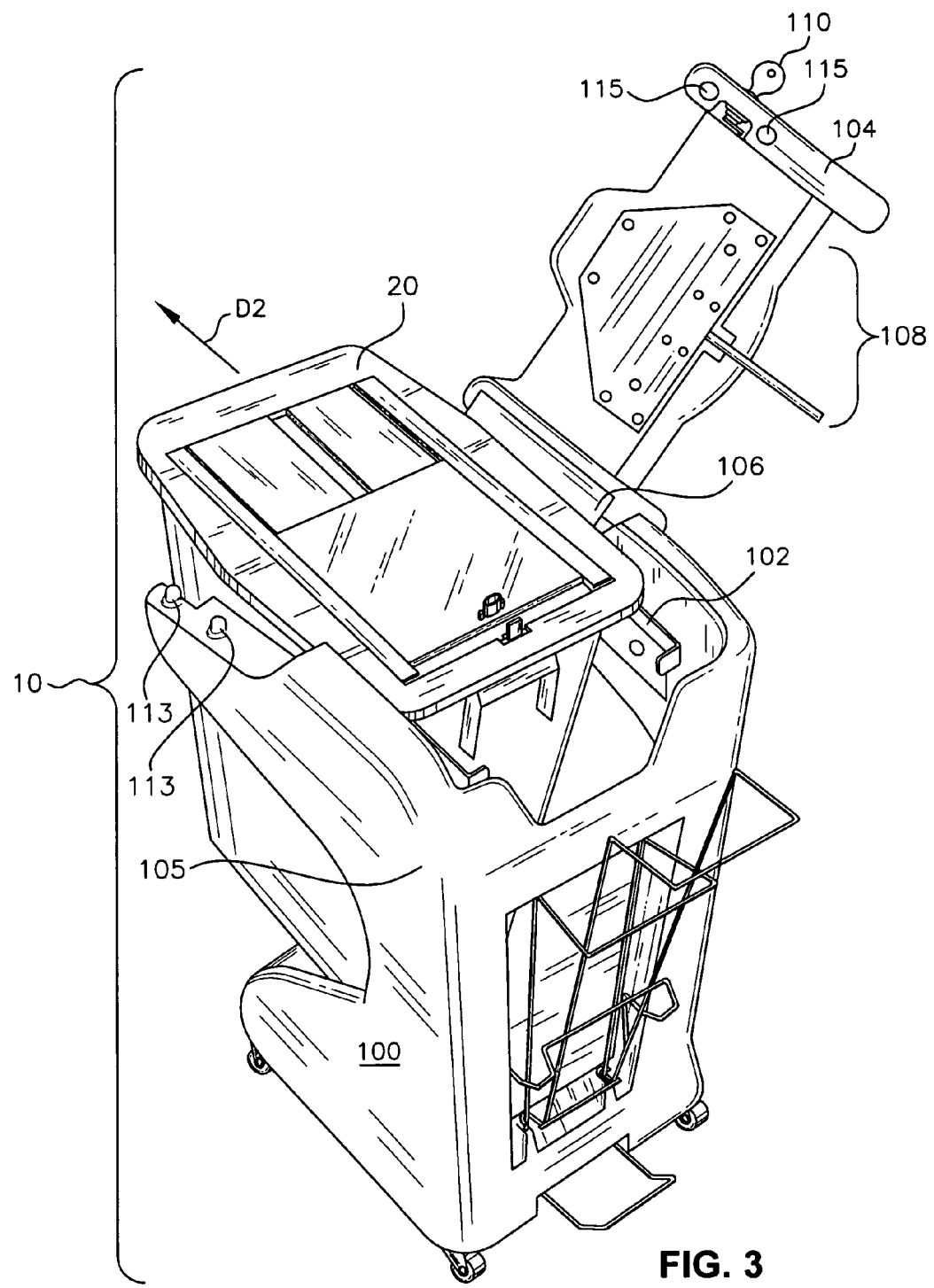
FIG. 3 is a perspective view of the container system illustrated in FIG. 1, as the container illustrated in FIG. 2 is being inserted into or withdrawn from a carrier component of the container system illustrated in FIG. 1.

Referring now to FIG. 3, the removal of the medical waste container 20 from the carrier 100 is illustrated. A body component 105 of the carrier 100 includes a pair of opposed guide rails 102 (only one shown in FIG. 3) in order to support the medical waste container 20 when it is positioned within the interior defined by the carrier 100. More specifically, the guide rails 102 provide a pair of supports against which the lip of the receptacle 22 and/or skirt of the lid 24 can rest. The container 20 can therefore be suspended and/or supported by the carrier 100.

The carrier 100 also includes a hood component 104 that is coupled by means of a hinge 106 to the body 105 of the carrier 100. The hinge 106 makes it possible to rotate the hood 104 with respect to the body 105 so that the hood 104 can be moved between an opened position (as shown in FIG.3) and a closed position (as shown in FIG. 1) The view provided in FIG. 3 also reveals a door retractor assembly 108, which is used to open and close the door 26 of the medical waste container 20, as will be described in further detail later.

When the hood 104 is rotated by means of the hinge 106 into a closed position (as shown in FIG. 1), removal of the medical waste container 20 from the carrier 100 is prevented. Also, a lock 110 is preferably provided on the hood 104 in order to lock the hood 104 in a closed position with respect to the body 105 of the carrier 100. Lock 110 can be a simple key lock, wherein rotation of the key brings about (or releases) engagement between the hood 104 and the body 105.

When the medical waste container 20 is desired to be removed from the carrier 100 (e.g., when the container 20 is filled with medical waste), it can be removed from the carrier 100 by unlocking the lock 110 on the hood 104, rotating the hood 104 from the closed position shown in FIG. 1 to the opened position shown in FIG. 3 by virtue of the hinge 106, and removing the medical waste container 20 from the carrier 100 in the direction designated by the arrow D2 in FIG. 3. The removal procedure can be reversed in order to introduce the medical waste container 20, or a replacement container 20, into the interior defined by the carrier 100.

The body 105 of the carrier 100 includes a pair of detents 113 that are positioned to mate with a corresponding pair of recesses 115 in the hood 104. The mating engagement of detents 113 and recesses 115 provides for alignment between the hood 104 and the body 105 when the hood 104 is being closed.

Figure 4:
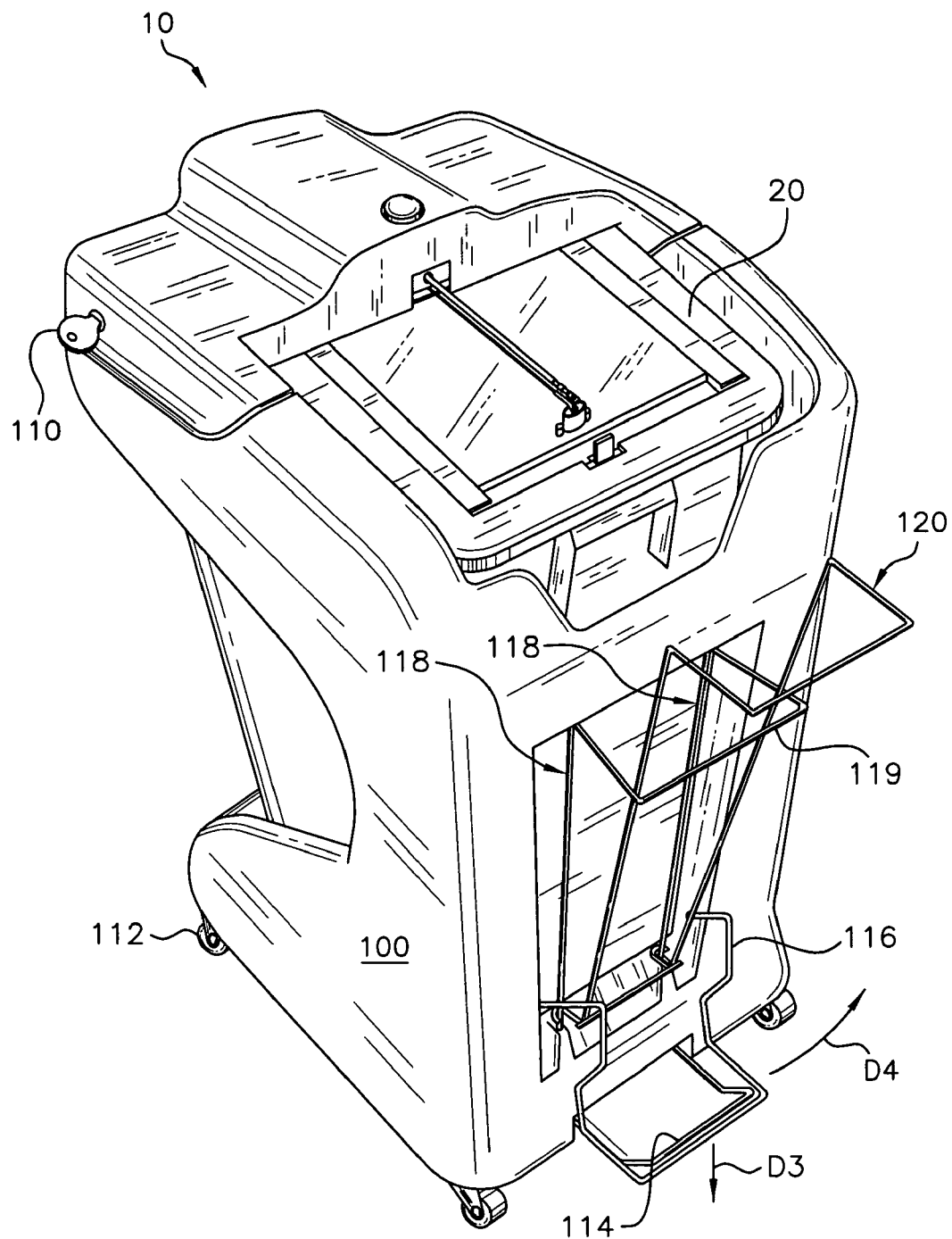
FIG. 4 is a perspective view of a base portion of the container system illustrated in FIG. 1.

Referring now to FIG. 4, a lower portion of the medical waste container system 10 is illustrated. The carrier 100 of the system 10 includes a lever 114, such as a foot pedal for example, in order to open and close the door 26 of the medical waste container 20. More specifically, the lever 114 is depressed downwardly by the foot of a user in the direction designated in FIG. 4 by the arrow D3. As will be described later in further detail, a cable coupled to the lever 114 runs from the lever, extends through the interior of the hollow body 105 of the carrier 100, and is coupled to a mechanism (arm control assembly 200 shown in FIG. 7) for opening and closing the door 26 of the medical waste container 20.

Although the foot pedal version of lever 114 shown in FIG. 4 can be replaced by a hand operated lever, the preferred operation of the lever 114 by the foot of a user obviates the need for the user to use his or her hand to contact the medical waste container system 10 in order to open the door 26. Instead, the user merely depresses the lever 114 with his or her foot to open the container 20.

Another preferred feature of the medical waste container system 10 is a mechanism for preventing a user from depressing the lever 114. It has been discovered that such a mechanism helps to prevent unauthorized users from opening the medical waste container by mere operation of the lever 114. Also, it has been discovered that such a mechanism helps to prevent authorized users from operating the lever 114 inadvertently. For example, when the waste container 20 is filled and no additional waste should be introduced into the receptacle 22, a mechanism for preventing a user from depressing the lever 114 helps prevent the inadvertent introduction of additional waste.

In the exemplary embodiment illustrated in FIG. 4, a bracket 116 is mounted to the body 105 of the carrier 100 at its ends for rotation with respect to the body 105 of the carrier 100. More specifically, the bracket 116 can be rotated from a retracted position (shown in FIG. 1) to the extended position shown in FIG. 4. It will be appreciated that, when the bracket 116 is in the locking position shown in FIG. 4, it is difficult or impossible for an unauthorized user to move the lever 114 in a direction indicated by the arrow D3. Inadvertent operation of the lever 114 by authorized users is also discouraged by the bracket 116 when it is in the position shown in FIG. 4.

In order to release the locking function of the bracket 116, the bracket 116 can be rotated in the direction indicated by the arrow D4 and returned to the position shown in FIG. 1. The bracket 116 can be operated by the foot of a user when it is located near the bottom of the carrier 100. Foot operation of the bracket 116 is preferred in order to reduce or eliminate hand contact between the user and the system 10. Alternatively, if the lever 114 and bracket 116 are located for hand operation, the user can position the bracket to block the lever by hand.

Referring now to FIGS. 5A–5F, one preferred embodiment of the body component 105 of the carrier 100 is illustrated. It should be noted that the body 105 could be formed in a wide variety of shapes, configurations, materials, sizes, and proportions. The shape and configuration of the body 105 are not dictated by its function. Instead, the configuration of the body 105 provides the carrier 100 with an ornamental appearance that is appealing to the eye.

The body 105 is preferably formed from plastic such as polyethylene (PE) for example, most preferably linear low density polyethylene (LLDPE), but a metallic body is also contemplated. Preferably, when the body 105 is formed from plastic, the body 105 is preferable formed by a molding process. Most preferably, the body 105 is formed by a rotational molding process.

Figure 5A:
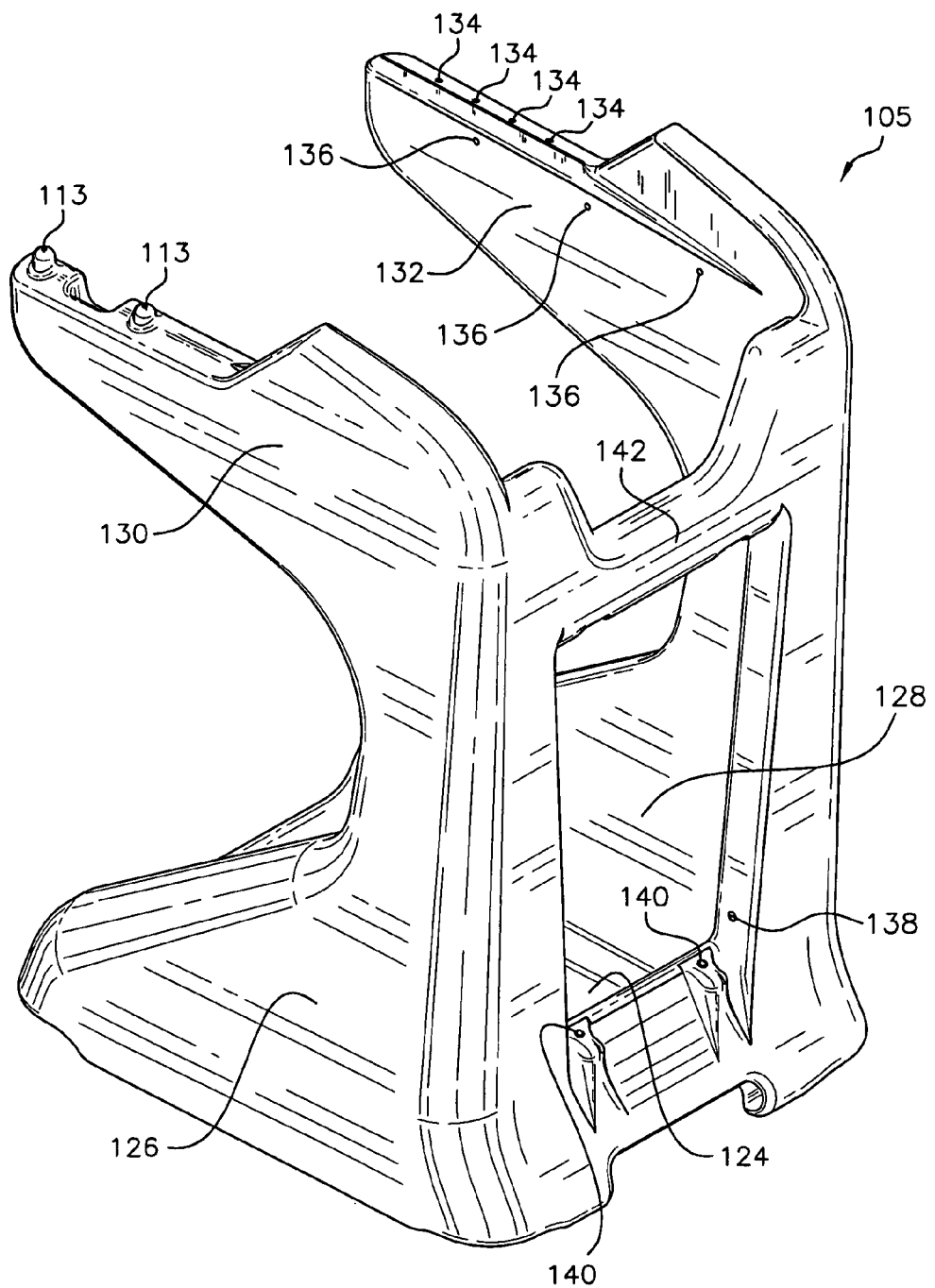
FIG. 5A is a perspective view of an embodiment of a body component of the container system illustrated in FIG. 1.

Referring specifically to the perspective view shown in FIG. 5A, the body 105 of the carrier 100 includes a base portion 124 to which the wheels 112 (shown in FIG. 4) can be mounted. The body 105 also includes a pair of lower side portions 126 and 128, a pair of upper side portions 130 and 132, and an upper front portion 142 that extends between the upper side portions 130 and 132.

The upper side portion 132 of the body 105 is provided with a series of hinge mounting holes 134 (four (4) shown), which facilitate the mounting of the hinge connecting the hood 104 to the body 105. The upper side portion 132 of the body 105 is also provided with a series of guide rail mounting holes 136 (three (3) shown) to facilitate the mounting of the guide rails 102 to the body 105. Only one set of guide rail mounting holes 136 is shown in FIG. 5A, and it will be understood that guide rail mounting holes 136 are also provided on the upper side portion 130 of the body 105.

Toward the base portion 124 of the body 105, a pair of bracket mounting holes 138 (only one shown in FIG. 5A) is provided for the mounting of terminal end portions of the bracket 116 shown in FIG. 4. The mounting holes 138 permit rotation of the bracket 116 with respect to the body 105 from a retracted position (FIG. 1) to an extended position (FIG. 4) and back again. Similarly, a pair of handle guide mounting holes 140 are provided near base portion 124 for mounting the lower portions of the handle guides 118. The mounting holes 144 for the upper portions of the handle guides 118 are shown in FIG. 5C and will be described later.

Figure 5B:
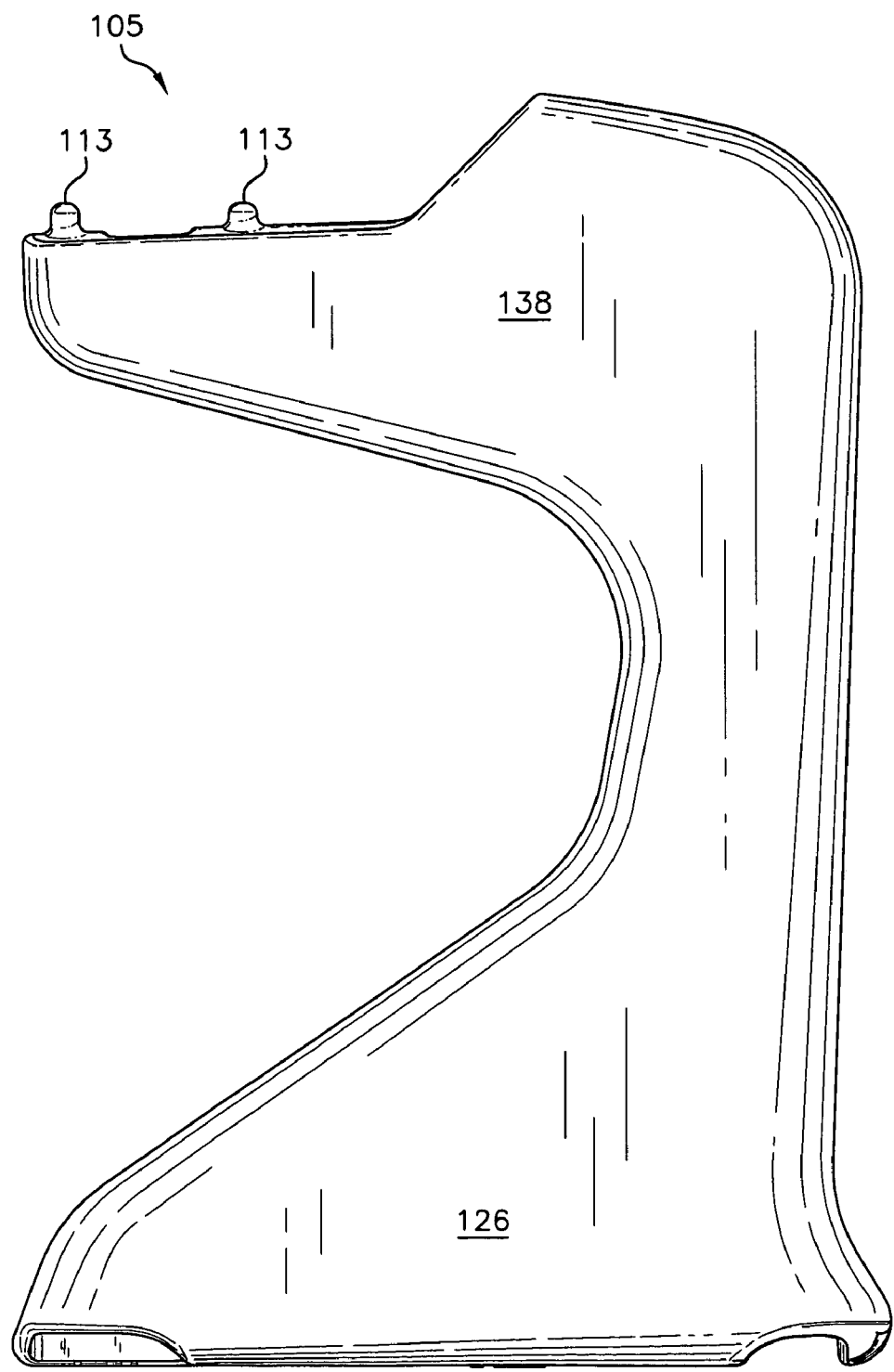
FIG. 5B is a left side view of the body component illustrated in FIG. 5A.

Referring now to FIG. 5B, a left-hand side view of the ornamental body 105 is illustrated. The ornamental body 105 extends from the lower side portion 126 to the upper side portion 130 in a series of contours.

Figure 5C:
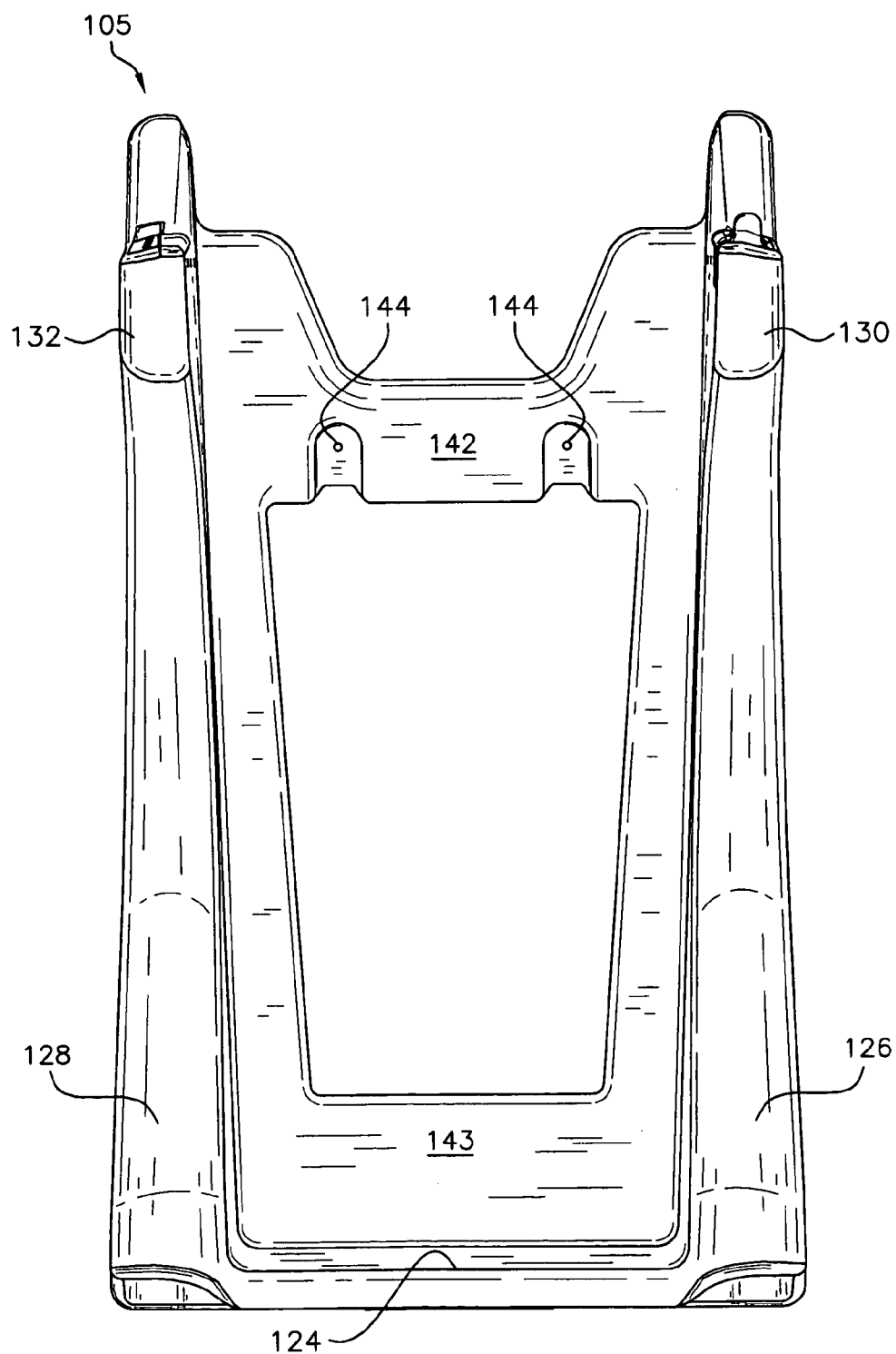
FIG. 5C is a rear view of the body component illustrated in FIG. 5A.

Referring to the rear view of the body 105 illustrated in FIG. 5C, the body 105 includes an ornamental upper front portion 142 that extends between the upper side portions 130 and 132. A pair of handle guide mounting holes 144 is provided on the upper front portion 142 in order to mount the upper portions of the handle guides 118 shown in FIG. 1. A lower front portion 143 of the body 105 extends between the lower side portions 126 and 128.

Figure 5D:
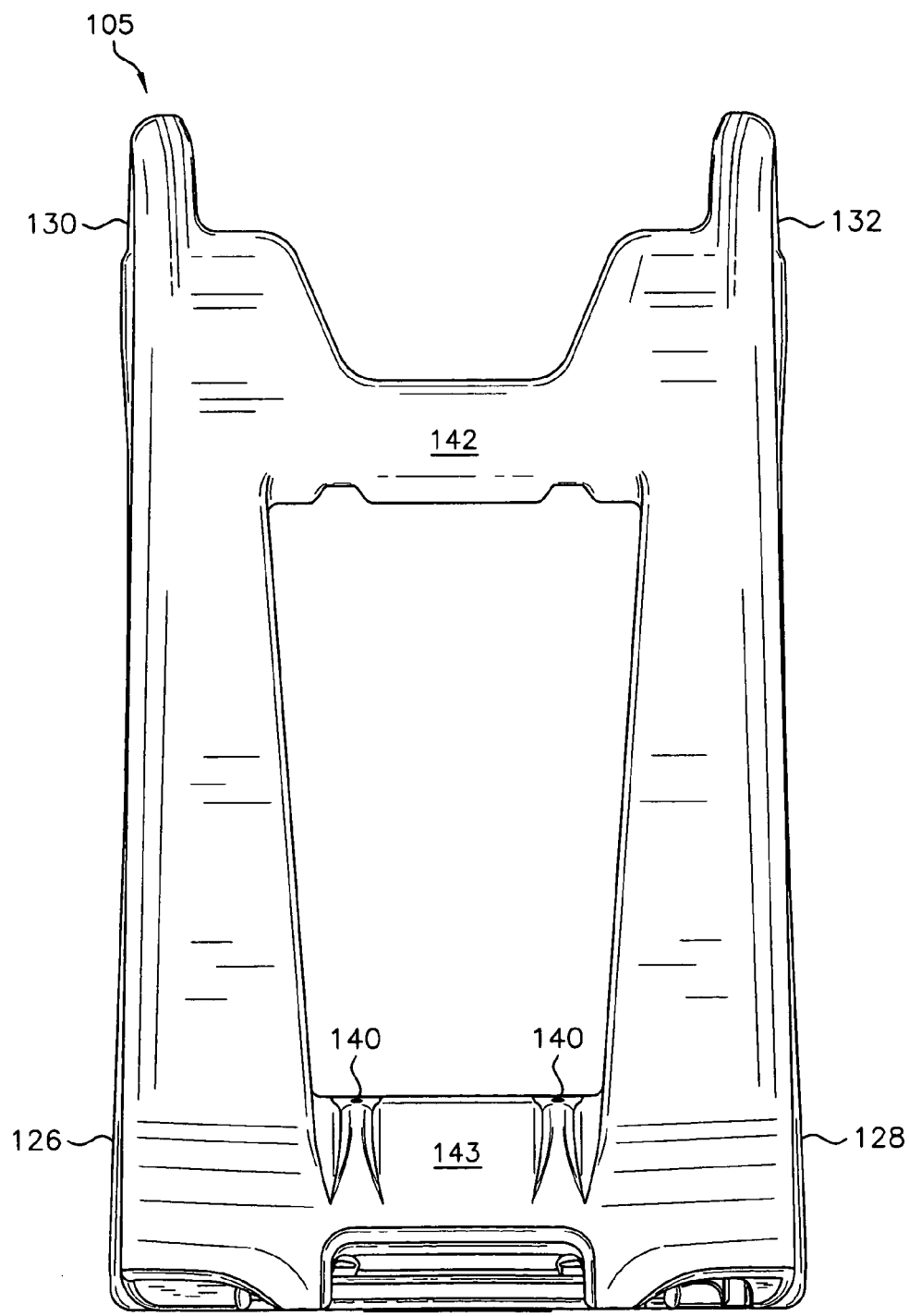
FIG. 5D is a front view of the body component illustrated in FIG. 5A.

FIG. 5D, which provides a front view of the body 105, illustrates additional ornamental features of the upper front portion 142 (extending between the upper side portions 130 and 132 of the body 105) and the lower front portion 143 (extending between lower side portions 126 and 128). Also, FIG. 5D illustrates another view of the handle guide mounting holes 140, which accommodate lower portions of the handle guides 118.

Figure 5E:
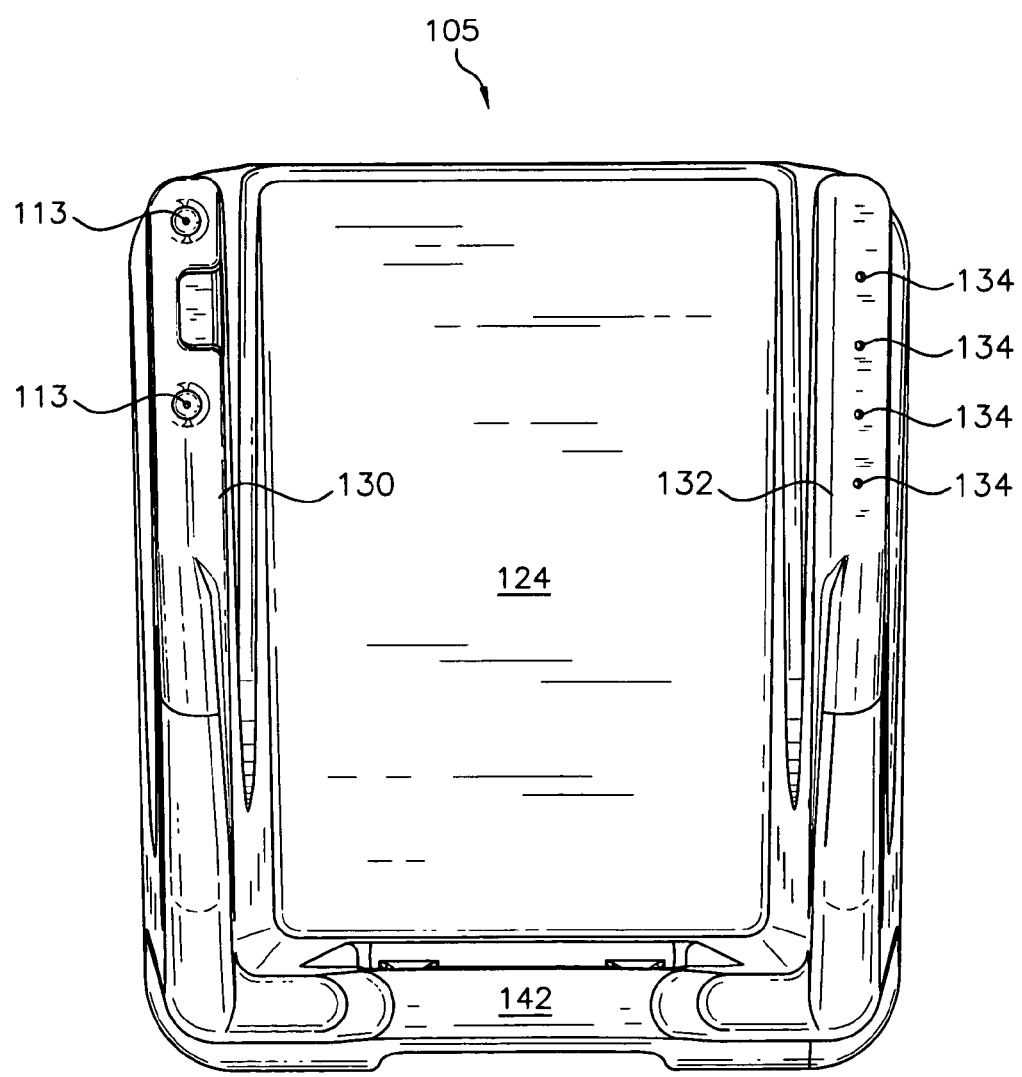
FIG. 5E is a top view of the body component illustrated in FIG. 5A.
Figure 5F:
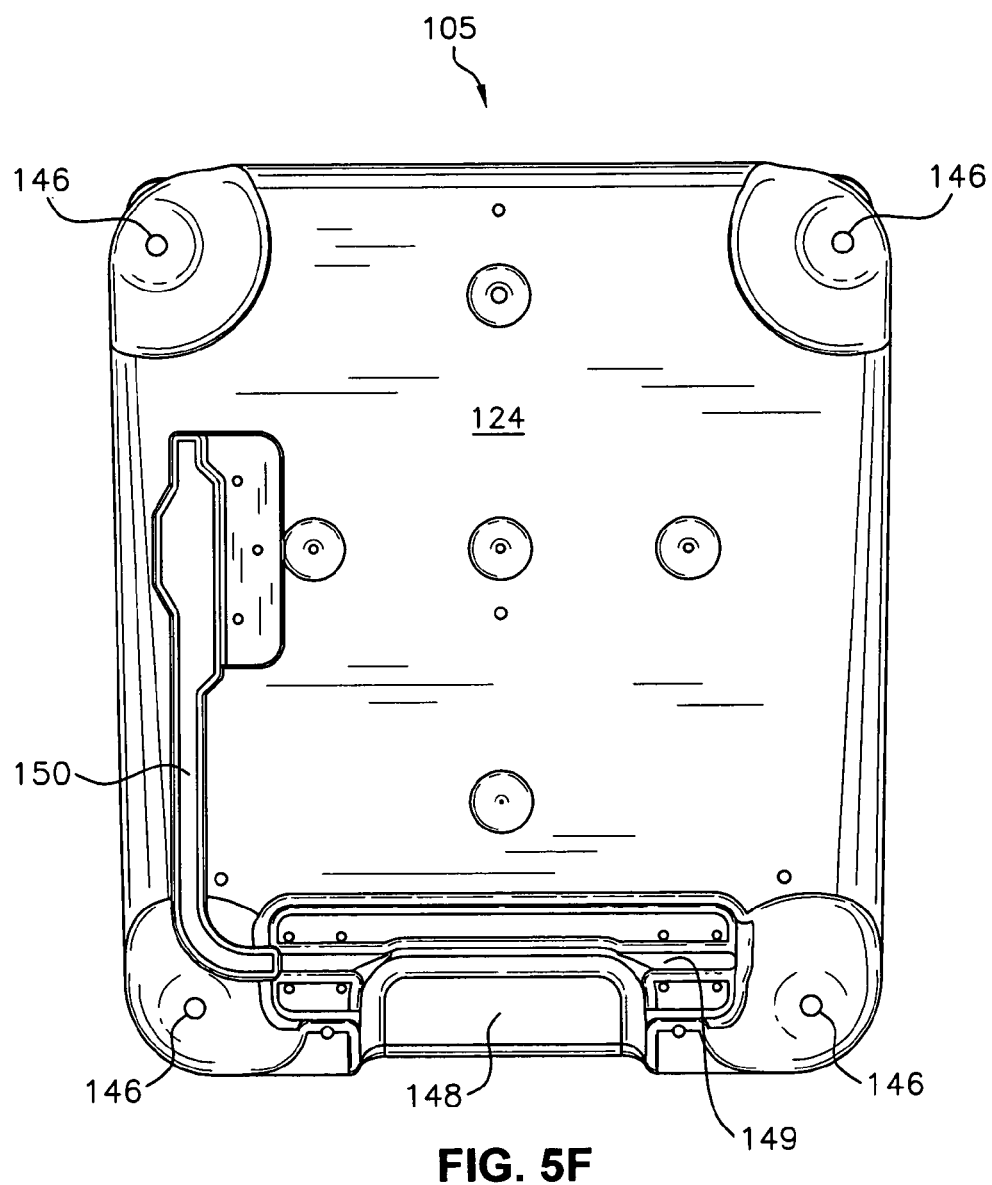
FIG. 5F is a bottom view of the body component illustrated in FIG. 5A.

Top and bottom views of the body 105 are illustrated in FIGS. 5E and 5F, respectively. FIG. 5E reveals additional ornamental features of the upper side portions 130 and 132 and the upper front portion 142 of the body 105. FIG. 5E also illustrates the hinge mounting holes 134 provided in upper side portion 132 of the body 105.

The bottom of body 105 is illustrated in FIG. 5F, which bottom includes four (4) wheel mounting holes 146 to facilitate the mounting of four (4) wheels 112 to the body 105 of the carrier 100. A recess 148 is provided in the bottom surface of the base portion 124 of the body 105 in order to accommodate the lever or foot pedal 114. The lever 114, when mounted to the base portion 124 of the body 105 as illustrated in FIG. 4, can reciprocate by rotation about an axis defined by a portion of the foot pedal that runs perpendicular to the direction in which the lever 114 is depressed. That portion of the lever 114 extends through a recess 149, and a pair blocks (not shown), each attached to the body 105 by a set of four (4) fasteners, captures the lever 114 so that its movement is limited to rotational movement about the axis of the recess 149.

Another portion of the lever 114 (not shown) extends perpendicularly with respect to axis about which the lever 114 rotates. More specifically, that portion of the lever 114 is oriented to extend through a channel 150 in the base portion 124. That portion of the lever 114 moves upwardly when the lever 114 is depressed by the foot of a user. By doing so, as will be described in further detail later, the lever 114 retracts a cable (not shown), thereby actuating the carrier 100 to open the door 26 of the medical waste container 20.

Referring now to FIGS. 6A–6C, preferred ornamental features of the hood component 104 of the carrier 100 will now be described. Referring first to the plan view shown in FIG. 6A, the hood 104 includes an aperture 152 through which a button (shown in FIG. 7) extends. As is illustrated in the right-side view shown in FIG. 6B, the hood 104 is preferably provided with an integral hinge stop 154. More specifically, hinge stop 154, which can be formed integrally with the hood 104, provides a limit to the hood's rotation when the hood 104 is fully opened. It will be understood that, when the hood 104 is opened to the position shown in FIG. 3, a surface of the hinge stop 154 will contact an upper, outer surface of the upper side portion 132, thereby preventing over-extension of the hinge. Finally, referring to the left-side view illustrated in FIG. 6C, the hood 104 is provided with an aperture 156 for receiving the lock 110.

The hood 104 also includes a container retainer portion 111, which prevents removal of the container 20 from the carrier 100 when the hood 104 is in the closed position. The retainer portion 111 is preferably formed integrally with the hood 104, but can take a wide variety of shapes, sizes and configurations.

Like the body 105, the hood 104 is preferably formed from plastic in a rotational molding process. It will be appreciated, however, that the configuration of the hood 104 can take a wide variety of forms, and that the contours selected for the hood 104 contributes to the overall ornamental appearance of the medical waste disposal system 10.

Figure 7:
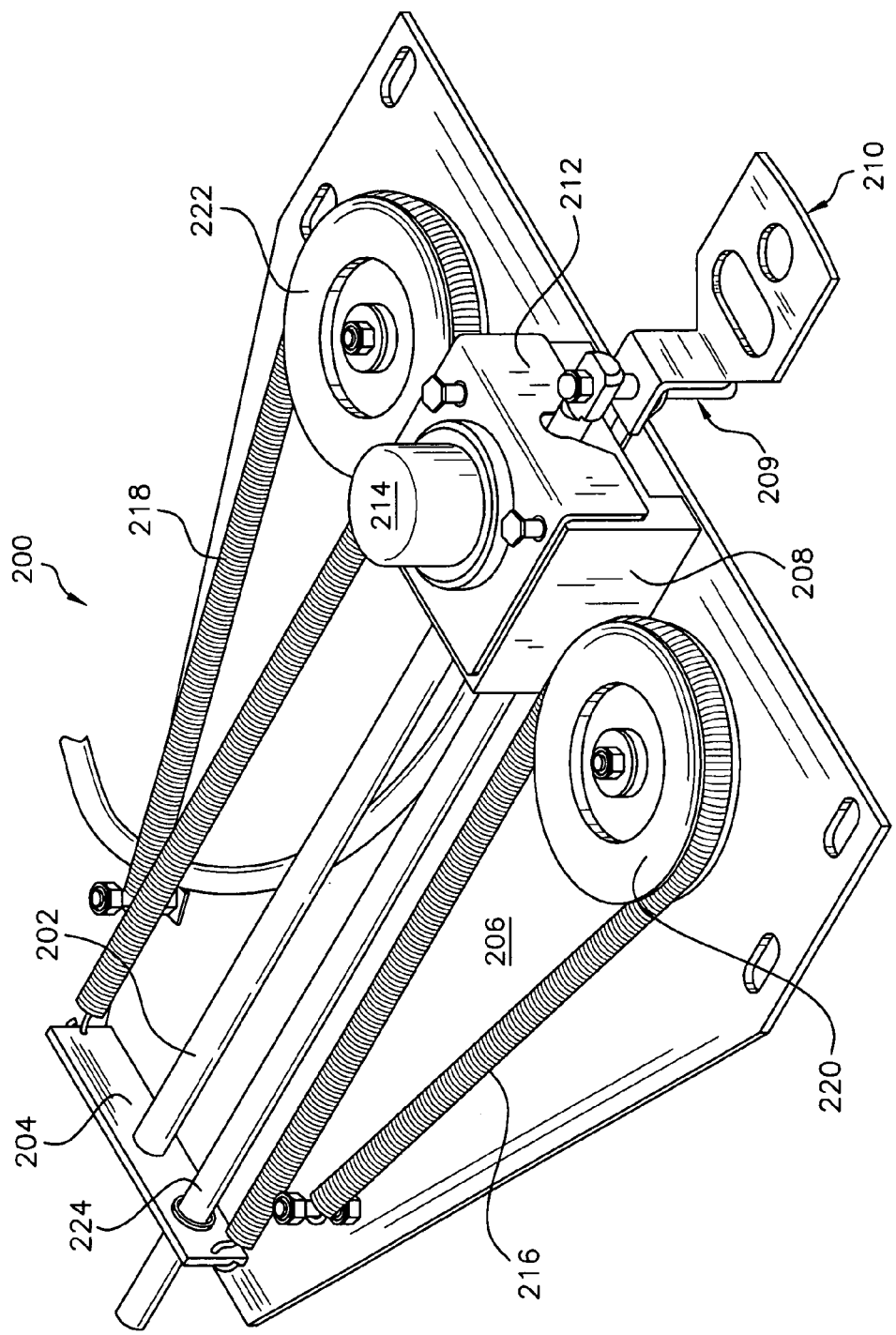
FIG. 7 is a perspective view of an embodiment of an extension or arm control assembly adapted for use in the container system illustrated in FIG. 1.

FIG. 7 illustrates details of one embodiment of a mechanism that can be employed to open and close the door 26 of the medical waste container 20 by operation of the lever 114. As is illustrated in FIGS. 3 and 7, an extension or arm control assembly 200 (FIG. 7) of the door retractor assembly 108 (FIG. 3) is mounted to the hood 104 of the carrier 100.

The arm control assembly 200 includes an extension or arm 202 that is mounted at its end to a bracket 204. The arm 202 extends parallel to a mounting plate 206 and extends through a mounting block 208 that is attached to the plate 206. A pin 209 is attached at the end of the arm 202 opposite from the bracket 204, and an optional bracket 210 is attached to the pin 209 for engagement with the door 26 of the lid 24 of the medical waste container 20. The pin 209 is provided to engage the door of the container. More specifically, the pin 209 extends into the upwardly extending recess 28 formed in the door 26 of the lid 24.

The bracket 210 is one embodiment of an extension of the arm 202 that can be used to adapt the arm control assembly 200 of the system 10 for use with a variety of containers. For example, containers having a configuration different from that of container 20 can be installed in the carrier 100, and an extension such as bracket 210 can be used to couple the arm 202 to the lid of the container. Accordingly, it will be understood that the door 26 of the lid 24 is reciprocated between opened and closed positions as the arm 202, pin 209, and optional bracket 210 of the arm control assembly 200 reciprocate with respect to the hood 104 of the carrier 100.

It is preferred for the carrier 100 to include a mechanism that enables a user of the system 10 to lock the door 26 of the medical waste container 20 in the opened position so that sharps can be introduced into the receptacle 22 of the medical waste container 20 without repeated openings of the container 20 or continuous depression of the foot pedal or lever 114. To accomplish this preferred function, the arm control assembly 200 is provided with a locking member 212 which is mounted for movement with respect to the block 208 so that the locking member 212 can be moved towards the plate 206 of the arm control assembly 200. Preferably, one or more springs are used in the arm control assembly 200, interposed between surfaces of the block 208 and the locking member 212, in order to bias the locking member 212 vertically away from the plate 206.

A button 214 is engaged to a surface of the locking member 212, preferably by means of an aperture (not shown) provided in the locking member 212, and is configured to extend upwardly through the aperture 152 provided in the hood 104 (FIG. 6A). A user of the system therefore has access to the button 214 so that the button 214 and locking member 212 can be depressed, thereby locking the arm 202 of the arm control assembly 200 in a retracted position in order to maintain the door 26 of the medical waste container 20 in the opened position.

Preferred features and the operation of the locking mechanism of the arm control assembly 200 will now be described in greater detail with general reference to FIGS. 7–9. As is illustrated in FIG. 8, the arm 202 of the arm control assembly 200 includes a mounting portion 226 to which the pin 209 is connected (e.g., by threaded fasteners). The arm 202 also includes a recess or a reduced diameter portion 228 and is spaced from the mounting portion 226.

Referring now to FIG. 9, which illustrates preferred features of the locking member 212 of the arm control assembly 200, the locking member 212 includes a pair of mounting holes 230 on a mounting portion 232 in order to facilitate the connection between the mounting member 212 and the block 208 of the arm control assembly 200.

The locking member 212 also includes a locking recess 234 on a locking portion 236. Locking recess of 234 of locking member 212 facilitates releasable engagement between the locking member 212 and the arm 202 of the arm control assembly 200 when the button 214 and locking member 212 are depressed by a user of the system 10 toward the plate 206 of the arm control assembly 200. More specifically, referring again to FIG. 7, the arm 202 of the arm control assembly 200 is preferably biased into the extended position (not shown in FIG. 7) wherein the arm 202 extends outwardly from the hood 104 as is shown in FIG. 3. More specifically, arm control assembly 200 includes a pair of coiled tension springs 216 and 218 which are mounted with respected to the plate 206 by means of two guides 220 and 222, respectively, which are mounted directly to the plate 206. A guide rod 224 may also be provided in the arm control assembly 200 in order to guide the end of the arm 202 that is connected to the bracket 204 as the arm 202 extends from the retracted position shown in FIG. 7 to the extended position shown in FIG. 3 and to keep the pin 209 in a vertical orientation.

By virtue of the springs 216 and 218 of the arm control assembly 200, the arm 202 is biased toward the extended position shown in FIG. 3 in that the springs 216 and 218 pull upon the bracket 204, thereby urging an extension of the arm 202 through the block 208 of the arm control assembly 200. When the button 214 and locking member 212 are depressed by a user of the system 10 while the arm 202 is in the retracted position shown in FIG. 7 (i.e., while the lever 114 is depressed and while the door 26 of the container is in the opened position), the locking recess 234 extends into the reduced diameter portion 228 of the arm 202 (FIG. 8). By virtue of the bias of the arm 202 towards the extended position after the lever 114 is released, it will be understood that a facing surface of the reduced diameter portion 228 is urged against a surface of the locking portion 236 of the locking member 212 that is adjacent to the locking recess 234.

Although not shown in FIG. 9, the hidden surface of the locking portion 236 is preferably provided with a counter-bore in the radiused portion of the locking recess 234, thereby facilitating greater frictional contact between the facing surface of the reduced diameter portion 228 of the arm 202 and the locking portion 236 of the locking member 212. The button 214 can be released by the user of the system 10, and the fictional engagement between the locking member 212 and the arm 202 will retain the arm 202 in the retracted position shown in FIG. 7.

When a user desires to release the arm 202, thereby allowing the carrier 100 to return the door 26 of the container 20 to the closed position, the user can actuate the lever or foot pedal 114 once again in order to release the engagement between the locking member 212 and the arm 202. More specifically, by actuating the lever 114 to retract the arm 202 farther into the hood 104, the fictional engagement between the locking member 212 and the arm 202 is broken, thereby permitting the button 214 and locking member 212 to return to their original position by action of the springs (not shown) that are interposed between the locking member 212 and the block 208.

Referring now to FIG. 10, a cable assembly 238 of the carrier 100 is illustrated. The cable assembly 238 is provided to couple the lever or foot pedal 114 to the arm 202 and/or pin 209 of the arm control assembly 200. More specifically, depressing the lever 114 downwardly in the direction D3 shown in FIG. 4 retracts the cable assembly 238 against the bias provided by springs 216 and 218 of the arm control assembly 200. In other words, as the lever 114 is actuated, the cable assembly 238 pulls the assembly of the arm 202, pin 209 and optional bracket 210 towards the retracted position shown in FIG. 7.

The cable assembly 238 preferably travels through a plastic conduit assembly in order to protect the cable and to reduce the wear between the cable and the components of the carrier 100. The cable assembly 238 extends through the body 105 of the carrier 100 from the lever 114 and through the hood 104 to the assembly of the arm 202, pin 209 and optional bracket 210.

One preferred embodiment of the cable assembly 238 is illustrated in FIG. 10. The cable assembly 238 includes an eyelet 240 connected to a lubricated metallic cable 242. The lubricated cable 242 extends through a conduit assembly including a pair of threaded conduit fittings 244, a plastic conduit 246, external tooth lockwashers 248, and jam nuts 250. The lubricated cable 242 extends outwardly from the opposite end of the conduit assembly and terminates at another eyelet 252. It will be understood that one end of the cable assembly 238 (e.g., eyelet 240 or 252) is coupled to the lever 114, and the other end of the cable assembly 238 (e.g., eyelet 252 or 240) is coupled to the arm control assembly 200. Accordingly, the cable assembly 238 couples the lever 114 to the arm control assembly 200 so that the depression of the lever 114 by a user of the system 10 brings about the retraction of the arm 202 of the arm control assembly 200 into the hood 104.

The operation of the medical waste container system 10 will now be described with general reference to FIGS. 1–10. A medical waste container 20 is introduced into the interior region defined by the carrier 100 by releasing the lock 110 on the hood 104, rotating the hood 104 by means of the hinge 106 to open the hood 104, sliding the medical waste container 20 into the interior region defined by the carrier 100 until a portion of the medical waste container 20 is supported by the guide rails 102 of the carrier 100, closing the hood 104, and engaging the lock 110, thereby locking the medical waste container 20 within the carrier 100.

In order to remove a filled medical waste container 20 from the carrier 100, the foregoing steps are substantially reversed. Specifically, the lock 110 on the hood 104 is disengaged, the hood 104 is again rotated by means of the hinge 106 into an open position, and the filled medical waste container 20 is then removed in the direction D2 shown in FIG. 3.

In order to open the medical waste container 20 using the system 10 (e.g., in order to deposit waste in the receptacle 22 of the container 20), the lever or foot pedal 114 is depressed by a user in a direction D3, thereby causing the arm 202 to retract into the hood 104 of the carrier 100 and causing the door 26 of the medical waste container 20 to slide into the opened position. Medical waste can then be deposited through the opening in the lid 24 of the medical waste container 20 for receipt in the receptacle 22.

In order to lock the door 26 of the medical waste container 20 in the open position after the depression of the lever 114 in the direction D3, the button 214 of the arm control assembly 200 can be depressed by the user and the lever 114 can be released in order to bring about engagement between the locking member 212 of the arm control assembly 200 and a surface of the reduced diameter portion 228 of the arm 202 of the arm control assembly 200. While the medical waste container 20 is locked in this opened position, a user of the system 10 need not depress the lever 114 (which will remain in the depressed position by virtue of the cable assembly 238 and the engagement between the locking member 212 and the arm 202), and the user can deposit medical waste in the medical waste container 20 through the open door 26.

In order to release the button 214 of the arm control assembly 200, thereby releasing the arm 202 and bringing about closure of the door 26, a user can depress the lever 114 farther. By doing so, the frictional interengagement between the locking member 212 and the arm 202 of the arm control assembly 200 is released so that the arm 202 can be extended from the hood 104, thereby allowing movement of the door 26 to the closed position as the lever 114 is released by the user (by virtue of the bias provided by the springs 216 and 218).

In order to prevent unauthorized or unintended use of the system 10 by operation of the lever 114, the bracket 116 can be rotated downwardly to a position corresponding to the lever 114 as is illustrated in FIG. 4. When in that position, the bracket 116 prevents an individual from depressing the lever 114 in the direction D3. Rotation of the bracket 116 upwardly (into the position shown in FIG. 1) permits operation of the lever 114.

Although this invention has been described with reference to particular embodiments selected for illustration in the Figures, it will be appreciated that many variations and modifications can be made to the system 10 and the components thereof without departing from the spirit or the scope of this invention. The ornamental appearance of the body 105 and hood 104 of the carrier 100 can be modified into a large number of possible configurations. Also, the materials used to form the hood 104 and body 105, as well as the manufacturing techniques used to form those components, can also be modified. Although the body 105 and hood 104 are preferably formed from plastic using a rotational molding technique, metallic and other materials can be used and the body and hood can be formed using other manufacturing techniques.

It will also be appreciated that the mechanism used to couple the lever 114 to the arm 202 can be varied within the scope of this invention. For example, the flexible cable can be replaced with a rigid linkage. Also, the location and form of the lever 114 can be changed. While the lever 114 preferably takes the form of a foot pedal located near the base of the carrier 100, the lever can also be a hand-operated lever located towards an upper portion of the carrier 100.

Additional variations can also be made within the scope of this invention, which is defined separately in the following claims:

What is claimed:

1. A modular container system comprising:
    a container having a door mounted for sliding reciprocation along a substantially horizontal path between opened and closed positions when the container is substantially upright; and
    a carrier comprising a body receiving the container and an arm coupled to said body for reciprocal extension along a longitudinal axis of said arm between an extended position and a retracted position with respect to said body, said axis of said arm being oriented substantially parallel to said path of said door of said container, said arm engaging said door of said container, and said reciprocal extension of said arm reciprocating said door of said container along said path between said opened and closed positions.

2. The container system of claim 1 wherein said carrier further comprises a flexible member coupled to said arm, wherein said arm is reciprocally extended or retracted along said axis by a tension applied to said flexible member.

3. The container system of claim 1 wherein said carrier further comprises a biasing member coupled to said arm to bias said arm toward said extended position or said retracted position, wherein said arm is reciprocally extended or retracted along said axis against said bias of said biasing member.

4. The container system of claim 3 wherein said biasing member comprises a spring.

5. The container system of claim 4 wherein said arm is biased by said biasing member toward said extended position.

6. The container system of claim 2 wherein said flexible member comprises a cable.

7. The container system of claim 6 wherein said carrier further comprises a lever pivotally coupled to said body, wherein tension is applied to said flexible member by actuation of said lever.

8. The container system of claim 7 wherein said carrier further comprises a locking bracket coupled to said body for reciprocation between a locked position, wherein said locking bracket prevents said lever from pivoting to open said door of said container, and an unlocked position, wherein said lever may pivot to open said door of said container.

9. The container system of claim 8 wherein the body of said carrier further comprises a body portion configured to support said container and a hood pivotally coupled to said body portion to pivot between a closed position wherein said hood restrains said container within said body portion and an open position wherein said container may be removed from said body portion.

10. The container system of claim 9 wherein said carrier further comprises a lock positioned for locking said hood in said closed position with respect to said body portion.

11. The container system of claim 10 wherein said lock is lockable and unlockable by use of a key.

12. The container system of claim 9 wherein said arm extends from said hood for reciprocal movement with respect to said hood.

13. The container system of claim 9 wherein said carrier further comprises a biasing member coupled to said arm and to said hood to bias said arm toward said extended position or said retracted position with respect to said hood, wherein said arm is reciprocally extended or retracted along said axis against said bias of said biasing member.

14. The container system of claim 1 wherein said carrier further comprises a locking member for locking said arm in said retracted position.

15. The container system of claim 14 wherein said arm has a shoulder portion which is engaged by said locking member to lock said arm in said retracted position.

16. The container system of claim 15 wherein said locking member is coupled to said body for reciprocal movement between an engaged position in which said arm is locked in said retracted position and a disengaged position in which said arm is free to move between said extended and retracted positions.

17. A container system comprising:
    a container having a door mounted for reciprocation between opened and closed positions; and
    a carrier holding said container, said carrier comprising:
        a body portion at least partially defining a cavity receiving said container;
        a hood portion coupled to the body portion and extending over at least a portion of said container; and
        an arm coupled to said hood for reciprocal movement with respect to said hood, said arm engaging said door of said container, and said reciprocal movement of said arm reciprocating said door of said container between said opened and closed positions.

18. A container system comprising:
    a container having a door mounted for reciprocation between opened and closed positions; and
    a carrier holding said container, said carrier having:
        a body portion at least partially defining a cavity receiving the container;
        a hood coupled to the body portion and extending over at least a portion of the container;
        an arm coupled to said hood for reciprocal movement with respect to said hood between an extended position when the door of the container is in the closed position and a non-extended position when the door of the container is in the opened position, said arm being engaged to the door of the container and adapted to reciprocate the door of the container between the closed and opened positions; and
        a spring coupled to the hood and to the arm for biasing the arm toward the extended position.

19. A container system comprising:
    a container having a door mounted for reciprocation between opened and closed positions; and
    a carrier receiving said container, said carrier having:
        a body portion;

a rotatable hood configured to cover at least a portion of the container when the rotatable hood is in a first position; and an arm coupled for reciprocal movement with respect to said rotatable hood along an axis of said arm, said arm having a first portion coupled to the rotatable hood with a longitudinal axis substantially parallel to the reciprocal movement and a second portion angled with respect to the first portion and engaging a surface of the door when the rotatable hood is in the first position.

20. A container system comprising:

a container having a door mounted for reciprocation between opened and closed positions; and a carrier holding said container, said carrier having:
 a body portion at least partially defining a cavity receiving the removable container;
 a hood coupled to the body portion and rotatable to a first position and a second position, said hood covering at least a portion of the container, thereby inhibiting removal of the container when the hood is in the first position and allowing removal of the container when the hood is in the second position; and
 a keyed lock for locking said hood in said first position with respect to said body portion.

21. A container system comprising:

a container having a door mounted for reciprocation between opened and closed positions; and a carrier holding said container, said carrier having:
 a body portion receiving the container, said body portion being formed from rotationally-molded plastic;
 a hood coupled to the body portion and extending over at least a portion of the container; and
 an arm coupled for reciprocal movement with respect to said hood, said arm engaging the door of the container, and said reciprocal movement of said arm reciprocating the door of the container between the opened and closed positions.

* * * * *

UNITED STATES PATENT AND TRADEMARK OFFICE
CERTIFICATE OF CORRECTION

PATENT NO. : 7,114,629 B2 Page 1 of 1
APPLICATION NO. : 09/845976
DATED : October 3, 2006
INVENTOR(S) : Robert Joseph Panek, Jr.

It is certified that error appears in the above-identified patent and that said Letters Patent is hereby corrected as shown below:

Colunm 2, line 12, "than" should be --that--

Signed and Sealed this

Twenty-seventh Day of February, 2007

JON W. DUDAS
*Director of the United States Patent and Trademark Office*